(12) United States Patent
Stoddard et al.

(10) Patent No.: US 12,239,337 B2
(45) Date of Patent: *Mar. 4, 2025

(54) ENDOSCOPIC INSTRUMENT

(71) Applicant: Covidien LP, Mansfield, MA (US)

(72) Inventors: Robert B. Stoddard, Steamboat Springs, CO (US); James S. Cunningham, Boulder, CO (US); William J. Dickhans, Longmont, CO (US); Russell D. Hempstead, Lafayette, CO (US); Eric R. Larson, Boulder, CO (US); Duane E. Kerr, Loveland, CO (US); William H. Nau, Jr., Longmont, CO (US); Anthony B. Ross, Boulder, CO (US); John J. Kappus, Boulder, CO (US)

(73) Assignee: Covidien LP, Mansfield, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/347,038

(22) Filed: Jul. 5, 2023

(65) Prior Publication Data

US 2023/0346410 A1 Nov. 2, 2023

Related U.S. Application Data

(60) Division of application No. 16/858,914, filed on Apr. 27, 2020, now Pat. No. 11,730,504, which is a
(Continued)

(51) Int. Cl.
*A61B 17/29* (2006.01)
*A61B 17/00* (2006.01)
(Continued)

(52) U.S. Cl.
CPC ...... *A61B 17/29* (2013.01); *A61B 2017/0046* (2013.01); *A61B 2017/00734* (2013.01);
(Continued)

(58) Field of Classification Search
CPC ...... A61B 2017/292; A61B 2017/2931; A61B 2017/2929; A61B 2017/293;
(Continued)

(56) References Cited

U.S. PATENT DOCUMENTS

| 4,258,716 A | 3/1981 | Sutherland |
| 4,760,848 A | 8/1988 | Hasson |

(Continued)

FOREIGN PATENT DOCUMENTS

| DE | 10064623 C1 | 8/2002 |
| DE | 69814283 T2 | 3/2004 |

(Continued)

OTHER PUBLICATIONS

Australian Examination Report No. 1 corresponding to counterpart Int'l Appln. No. AU 2013207564 dated Jun. 8, 2017.
(Continued)

*Primary Examiner* — Katherine H Schwiker (57) ABSTRACT

An endoscopic instrument is provided and includes a housing including an elongated shaft assembly extending distally therefrom. The elongated shaft assembly includes inner and outer shaft members. The inner and outer shaft members are removably coupled to the housing and the outer shaft member is movable with respect to the inner shaft member. An end effector is operably supported at the distal end of the outer shaft member and includes a pair of jaw members configured for treating tissue. A bushing operably couples to the inner and outer shaft members of the shaft assembly and selectively and releasably couples to the housing. The bushing includes one or more mechanical interfaces configured to engage one or more slots defined through the inner shaft member and one or more slots defined through the outer shaft member to release the inner and outer shaft members from the housing.

14 Claims, 9 Drawing Sheets

Related U.S. Application Data continuation of application No. 14/881,310, filed on Oct. 13, 2015, now Pat. No. 10,639,053, which is a division of application No. 13/838,945, filed on Mar. 15, 2013, now Pat. No. 9,161,769.

(60) Provisional application No. 61/677,348, filed on Jul. 30, 2012.

(51) Int. Cl.
    *A61B 17/32* (2006.01)
    *A61B 18/00* (2006.01)
    *A61B 18/14* (2006.01)

(52) U.S. Cl.
    CPC ... *A61B 17/2909* (2013.01); *A61B 2017/2925* (2013.01); *A61B 2017/2929* (2013.01); *A61B 2017/293* (2013.01); *A61B 2017/2931* (2013.01); *A61B 2017/2946* (2013.01); *A61B 17/320068* (2013.01); *A61B 2017/320095* (2017.08); *A61B 2018/0019* (2013.01); *A61B 2018/0063* (2013.01); *A61B 2018/00994* (2013.01); *A61B 18/1445* (2013.01)

(58) Field of Classification Search
    CPC ...... A61B 2017/2909; A61B 2017/291; A61B 2017/2946; A61B 2017/00734; A61B 2017/0046; A61B 2017/00464; A61B 2017/00477
    See application file for complete search history.

(56) References Cited

U.S. PATENT DOCUMENTS

| | | |
|---|---|---|
| 5,222,973 A | 6/1993 | Sharpe et al. |
| 5,290,302 A | 3/1994 | Pericic |
| 5,634,918 A | 6/1997 | Richards |
| 6,051,011 A | 4/2000 | Weidenbenner |
| 6,352,532 B1 | 3/2002 | Kramer et al. |
| 6,391,046 B1 | 5/2002 | Overaker et al. |
| 6,425,910 B1 | 7/2002 | Hugueny et al. |
| 6,482,198 B2 | 11/2002 | Overaker et al. |
| 6,488,695 B1 | 12/2002 | Hickingbotham |
| 6,635,071 B2 | 10/2003 | Boche et al. |
| 6,730,076 B2 | 5/2004 | Hickingbotham |
| D491,268 S | 6/2004 | Hickingbotham |
| D497,427 S | 10/2004 | Hickingbotham |
| D504,176 S | 4/2005 | Vijfvinkel |
| 6,908,476 B2 | 6/2005 | Jud et al. |
| 7,600,405 B2 | 10/2009 | Maurer, Jr. et al. |
| 7,731,728 B2 | 6/2010 | Glaser |
| 8,444,664 B2 | 5/2013 | Balanev et al. |
| 9,161,769 B2 | 10/2015 | Stoddard et al. |
| 9,351,753 B2 | 5/2016 | Balanev et al. |
| 10,639,053 B2 | 5/2020 | Stoddard et al. |
| 2006/0025793 A1 | 2/2006 | Gibson et al. |
| 2006/0079879 A1 | 4/2006 | Faller et al. |
| 2006/0241532 A1 | 10/2006 | Murakami |
| 2006/0259070 A1 | 11/2006 | Livneh |
| 2008/0154299 A1 | 6/2008 | Livneh |
| 2008/0167680 A1 | 7/2008 | Voegele et al. |
| 2008/0208195 A1 | 8/2008 | Shores et al. |
| 2009/0088667 A1 | 4/2009 | Masuda |
| 2010/0106183 A1 | 4/2010 | Lee et al. |
| 2012/0116363 A1 | 5/2012 | Houser et al. |
| 2012/0150217 A1 | 6/2012 | Hickingbotham et al. |
| 2012/0239009 A1 | 9/2012 | Mollere et al. |
| 2012/0271347 A1 | 10/2012 | Kaercher |
| 2012/0310229 A1 | 12/2012 | Gregg |
| 2013/0030328 A1 | 1/2013 | Dycus et al. |
| 2013/0085419 A1 | 4/2013 | Stoddard et al. |
| 2013/0121366 A1 | 5/2013 | Misuchenko et al. |

FOREIGN PATENT DOCUMENTS

| | | |
|---|---|---|
| JP | 2000237204 A | 9/2000 |
| WO | 2012061640 A1 | 5/2012 |
| WO | 2012061641 A2 | 5/2012 |
| WO | 2012061646 A1 | 5/2012 |

OTHER PUBLICATIONS

Japanese Office Action corresponding to counterpart Int'l Appln. No. JP 2013-154526 dated Mar. 1, 2017.
Partial European Search Report corresponding to EP 13 17 8512.3, completed Nov. 21, 2013 and dated Nov. 29, 2013; (6 pp).
European Search Report dated May 12, 2014 issued in European Appln. No. 13178512.
Extended European Search Report corresponding to EP 14 19 7334.7, completed Feb. 5, 2015 and dated Feb. 12, 2015; (10 pp).
Canadian Office Action issued in corresponding Canadian Application No. 2,821,471 dated Mar. 8, 2019, 4 pages.

ENDOSCOPIC INSTRUMENT

CROSS-REFERENCE TO RELATED APPLICATIONS

This application is a divisional application of U.S. patent application Ser. No. 16/858,914, filed on Apr. 27, 2020, which is a continuation application of U.S. patent application Ser. No. 14/881,310, filed on Oct. 13, 2015, now U.S. Pat. No. 10,639,053, which is a divisional application of U.S. patent application Ser. No. 13/838,945, filed on Mar. 15, 2013, now U.S. Pat. No. 9,161,769, which claims the benefit of U.S. Provisional Patent Application Ser. No. 61/677,348, filed on Jul. 30, 2012, the entire contents of each of which being incorporated by reference herein.

FIELD

The present disclosure relates to endoscopic instruments and, more particularly, to endoscopic instruments including selectively removable shaft assemblies.

BACKGROUND

Endoscopic instruments are well known in the medical arts. For example, an electrosurgical endoscopic forceps (a closed forceps) is utilized in surgical procedures, e.g., laparoscopic surgical procedure, where access to tissue is accomplished through a cannula or other suitable device positioned in an opening on a patient. The endoscopic forceps, typically, includes a housing, a handle assembly including a movable handle, a shaft and an end effector assembly attached to a distal end of the shaft. The end effector includes jaw members configured to manipulate tissue, e.g., grasp and seal tissues. The endoscopic instrument may be configured to utilize one or more types of energies including, but not limited to, RF energy, microwave energy, ultra sound to treat tissue.

Another type of endoscopic instrument that may be utilized in laparoscopic surgical procedures is an ultrasonic endoscopic forceps. The ultrasonic endoscopic forceps is similar in configuration to the electrosurgical endoscopic forceps. Unlike the electrosurgical endoscopic forceps, however, the ultrasonic endoscopic forceps utilizes ultrasonic energy to treat tissue.

As is conventional with both of the above endoscopic instruments, the shaft of these instruments is, typically, rigidly attached to the endoscopic instrument, i.e., the shaft is non-removable from the housings of the respective instruments. Having an endoscopic instrument with a non-removable shaft may prove problematic during the operative life cycle of the endoscopic instrument. For example, if the endoscopic instrument is to be re-used, the entire device is, typically, sterilized via an autoclaving process or the like. As can be appreciated, sterilizing an endoscopic instrument with the shaft including the end effector attached may prove difficult. In particular, it may prove difficult to sterilize between small spaces of the shaft, e.g., spaces at a distal end of the shaft adjacent the end effector.

SUMMARY

In view of the foregoing, it may prove advantageous in the medical arts to provide endoscopic instruments that include selectively removable shaft assemblies.

In the drawings and in the descriptions that follow, the term "proximal," as is traditional, will refer to an end which is closer to the user, while the term "distal" will refer to an end that is farther from the user.

As used herein, "endoscopic instrument" generally refers to any surgical instrument that is configured for access into a body cavity. The endoscopic instrument may be configured to grasp tissue or may be configured to grasp and subsequently electrosurgically treat tissue, e.g., an electrosurgical endoscopic device. In the latter instance, the endoscopic instrument may be configured to couple to one or more suitable electrosurgical energy sources. Or, the endoscopic instrument may be battery powered. As it is used herein, "electrosurgical procedure" generally refers to any electrosurgical procedure involving any form of energy, such as, for example, microwave energy, radiofrequency (RF) energy, ultrasonic energy, thermal energy or combination thereof.

An aspect of the present disclosure provides an endoscopic instrument. The endoscopic instrument includes a housing including an elongated shaft assembly extending distally therefrom. The elongated shaft assembly has inner and outer shaft members. The inner and outer shaft members are removably coupled to the housing and the outer shaft member is movable with respect to the inner shaft member. An end effector is operably supported at the distal end of the outer shaft member and includes a pair of jaw members configured for treating tissue. A bushing may be operably coupled to the inner and outer shaft members of the shaft assembly and configured to selectively and releasably couple to the housing. In certain instances, the bushing may include one or more resilient fingers that are configured to engage one or more slots defined through the inner shaft member and one or more slots defined through the outer shaft member to release the inner and outer shaft members from the housing. In certain instances, slot(s) on the outer shaft member is/are longer than the slot(s) on the inner shaft member to allow the outer shaft member to translate with respect to the inner shaft member.

A spring carrier includes one or more resilient bosses that are configured to releasably engage one or more second slots defined through the outer shaft member at a proximal end thereof to release the inner and outer shaft members from the housing when the outer shaft member is rotated with respect to the spring carrier. The spring carrier is configured to provide axial movement of the outer shaft member when a handle assembly of the endoscopic instrument is actuated. In certain instance, the resilient boss(es) includes a chamfered edge that is configured contact an edge of the corresponding second slot to move the resilient boss(es) out of engagement with the corresponding second slot when the outer shaft member is rotated. The spring carrier may include a plurality of radial slots on a distal face thereof. The plurality of radial slots are configured to engage a corresponding plurality of mating features disposed on an interior wall of the housing when the spring carrier is in a forward-most position within the housing. Engagement between the plurality of radial slots and corresponding plurality of mating features prevents rotation of the spring carrier when outer shaft member is rotated.

An aspect of the present disclosure provides an endoscopic instrument. The endoscopic instrument includes a housing that includes an elongated shaft assembly extending distally therefrom. The elongated shaft assembly has inner and outer shaft members. The inner and outer shaft members are removably coupled to the housing and the outer shaft member is movable with respect to the inner shaft member. An end effector is operably supported at the distal end of the outer shaft member. A bushing is operably coupled to the inner and outer shaft members of the shaft assembly and is selectively and releasably coupled to the housing. The bushing includes a generally annular groove located at a proximal end thereof. A latch is operably disposed on the housing and is movable with respect thereto for selectively and releasably engaging the annular groove on the bushing to release the inner and outer shaft members from the housing.

The latch may include a pair of opposing arms. Each of the opposing arms may include a respective detent that seats within a corresponding pocket disposed within an interior wall of the housing. The detents may be seated within the pockets and configured to limit movement of the latch.

The latch may include an aperture that is configured to receive the bushing and the outer shaft member therethrough. Moreover, the latch may include a generally elongated slot therein that is configured to engage a corresponding detent disposed on a locking member that is positioned proximal the latch and movable therewith. In this instance, the locking member may be configured to couple the outer shaft member to a spring carrier configured to provide axial movement of the outer shaft member when a handle assembly of the endoscopic instrument is actuated. The outer shaft member may include a flange disposed at a proximal end thereof that is configured to engage the locking member.

An aspect of the instant disclosure provides an endoscopic instrument. The endoscopic instrument includes a housing that includes an elongated shaft assembly extending distally therefrom. The elongated shaft assembly has inner and outer shaft members. The inner and outer shaft members are removably coupled to the housing and the outer shaft member is movable with respect to the inner shaft member. A rotating assembly is operably coupled to the housing and is configured to rotate the inner and outer shaft members. A bushing is removably coupled to the rotating assembly and is operably coupled to the inner and outer shaft members and selectively and releasably coupled to the rotating assembly. An end effector is operably supported at the distal end of the outer shaft member. The bushing includes one or more mechanical interfaces that are configured to engage one or more slots defined through the inner shaft member and at least one slot defined through the outer shaft member to release the inner and outer shaft members from the housing.

The mechanical interfaces of the bushing may be in the form of one or more resilient fingers. In this instance, the at least one slot on the outer shaft member is longer than the at least one slot on the inner shaft member to allow the outer shaft member to translate with respect to the inner shaft member.

A spring carrier may be provided and may include at least one resilient boss. The resilient boss may be configured to releasably engage at least one second slot defined through the outer shaft member at a proximal end thereof and configured to release the inner and outer shaft members from the housing when the outer shaft member is rotated with respect to the spring carrier. The at least one resilient boss may include a chamfered edge that is configured to contact an edge of the corresponding second slot to move the at least one resilient boss out of engagement with the corresponding second slot when the outer shaft member is rotated. The spring carrier may be further configured to provide axial movement of the outer shaft member when a handle assembly of the endoscopic instrument is actuated. The spring carrier may include a plurality of radial slots defined on a distal face thereof. The plurality of radial slots may be configured to engage a corresponding plurality of mating features disposed on an interior wall of the housing when the spring carrier is moved to a forward-most position within the housing. Engagement between the plurality of radial slots and corresponding plurality of mating features prevents rotation of the spring carrier when outer shaft member is rotated.

The mechanical interfaces of the bushing may be in the form of one or more detents. In this instance, the bushing may include a generally annular groove that is located at a proximal end thereof.

A latch may be operably disposed on the housing and may be movable with respect thereto for selectively and releasably engaging the annular groove on the bushing to release the inner and outer shaft members from the housing. The latch may include a pair of opposing arms. Each of the opposing arms may include a respective detent that seats within a corresponding pocket disposed within an interior wall of the housing. The detents may be seated within the pockets and configured to limit movement of the latch. The latch may include an aperture that is configured to receive the bushing and the outer shaft member therethrough. The latch may include a generally elongated slot therein that is configured to engage a corresponding detent disposed on a locking member positioned proximal the latch and movable therewith. The locking member may be configured to couple the outer shaft member to a spring carrier configured to provide axial movement of the outer shaft member when a handle assembly of the endoscopic instrument is actuated. The outer shaft member may include a flange that is disposed at a proximal end thereof that is configured to engage the locking member.

BRIEF DESCRIPTION OF THE DRAWINGS

Various embodiments of the present disclosure are described hereinbelow with reference to the drawings, wherein.

DETAILED DESCRIPTION

Detailed embodiments of the present disclosure are disclosed herein; however, the disclosed embodiments are merely examples of the disclosure, which may be embodied in various forms. Therefore, specific structural and functional details disclosed herein are not to be interpreted as limiting, but merely as a basis for the claims and as a representative basis for teaching one skilled in the art to variously employ the present disclosure in virtually any appropriately detailed structure.

As noted above, it may prove useful in the medical arts to provide an endoscopic instrument that includes a selectively removable shaft assembly. In accordance with the instant disclosure, a selectively removable shaft assembly that may be configured for use with a variety of endoscopic surgical instruments is provided. The selectively removable shaft assembly includes a unique bushing configuration that couples to inner and outer shaft members of the shaft assembly to allow a user to remove the inner and outer shaft members from a housing of the endoscopic instrument. The unique bushing configuration also allows axial translation of the outer shaft member with respect to the inner shaft member.

Figure 1:
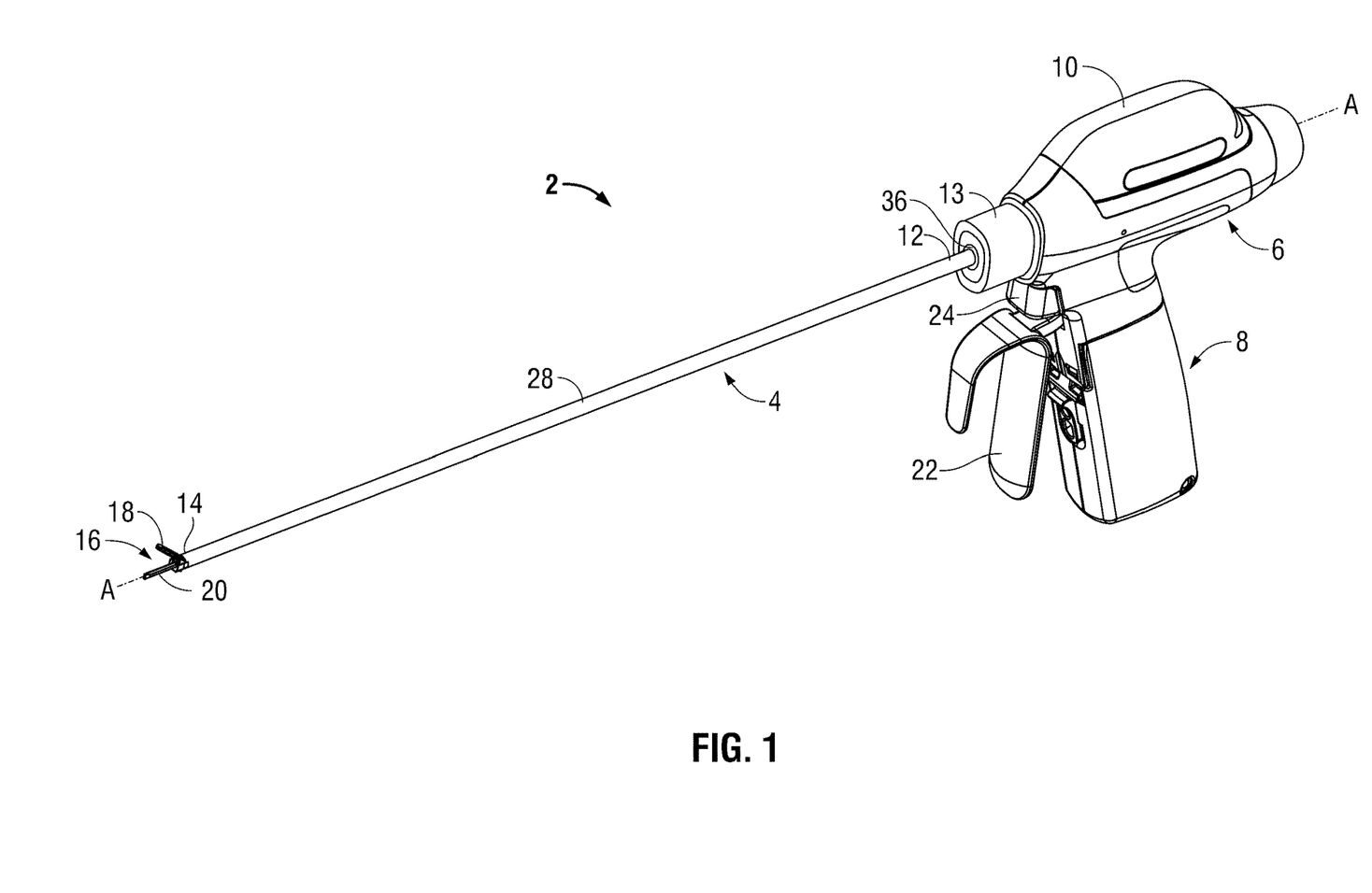
FIG. 1 is a side, perspective view of an endoscopic instrument including a selectively removable shaft assembly according to an embodiment of the present disclosure.

With reference to FIG. 1, an endoscopic instrument 2 that utilizes a selectively removable shaft assembly 4 according to an embodiment of the instant disclosure is illustrated. For illustrative purposes, the endoscopic instrument 2 that is configured for use with the shaft assembly 4 is a battery powered ultrasonic instrument 2 (e.g., an ultrasonic forceps 2). Briefly, forceps 2 includes a housing 6 that is configured to house one or more components, e.g., transducer, waveguide and electrical circuitry that is configured for electrical communication with a battery assembly 8 of the forceps 2. A proximal end of housing 6 is configured to releasably couple to an ultrasonic generator 10 and the battery assembly 8. A distal end of the housing 6 is configured to support and releasably couple to a proximal end 12 (FIGS. 1 and 2) of shaft assembly 4 that is releasably positionable within a rotating assembly 13. Shaft assembly 4 extends from housing 6 and defines a longitudinal axis "A-A" therethrough (FIG. 1). A distal end 14 of the shaft assembly 4 is configured to support an end effector 16 thereon. The operational parts of end effector 16 (e.g., jaw members 18 and 20) are movable relative to one another upon actuation of a movable handle assembly 22 coupled to housing 6.

In the illustrated embodiment, jaw member 20 serves as an active or oscillating blade and is configured to treat tissue. An activation button 24 places the forceps 2 in one or more modes of operation and generator 10 is configured to convert electrical energy produced by the battery assembly 8 into ultrasonic energy. More particularly, generator 10 includes a transducer (not explicitly shown) that is configured to convert electrical energy to mechanical energy that produces motion in a waveguide (not explicitly shown) that is in operative communication with the active jaw member 20.

Figure 2:
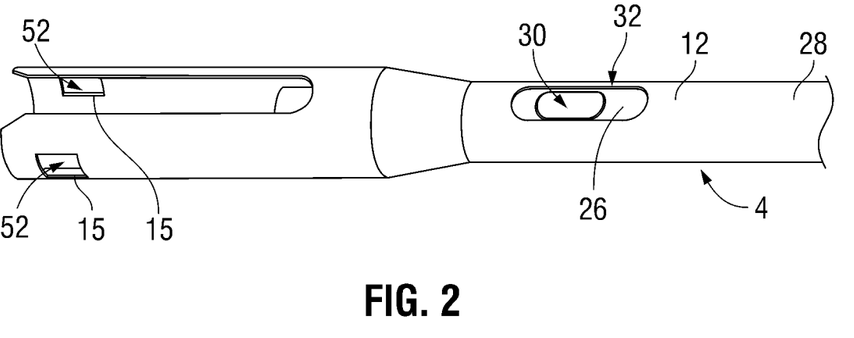
FIG. 2 is a side, perspective view of a proximal end of the shaft assembly depicted in FIG. 1 shown unattached from a housing of the endoscopic instrument.

With reference now to FIG. 2, the proximal end 12 of the shaft assembly 4 is illustrated to show the operative components of the shaft assembly 4. Shaft assembly 4 includes inner and outer shaft members 26 and 28 respectively. In the illustrated embodiment, the inner shaft member 26 encases an ultrasonic shaft (not explicitly shown). Unlike outer shaft member 28 which is movable axially along the longitudinal axis "A-A" to move jaw member 18, inner shaft 26 is fixed as it does not move axially to move jaw member 18. Rather, inner shaft 26 supports pivot points (not explicitly shown) for jaw member 18 to open and close. The ultrasonic shaft member is rigidly coupled to the housing 6 and is configured to house one or more components of the forceps 2, e.g., the waveguide and/or transducer therein. In some embodiments, however, the ultrasonic shaft may be configured to releasably couple to the housing 6.

Outer shaft member 28 is configured to support the jaw members 18 and 20 thereon (FIG. 1) and is configured to releasably couple to one or more components, e.g., a spring carrier 42 (FIG. 4), of the housing 6. Thus, after use, the inner shaft member 26 and outer shaft member 28 (including the jaw members 18 and 20 supported thereon) may be removed from the housing 6 so that the housing 6 including the ultrasonic shaft may be sterilized. As noted above, outer shaft 28 moves axially along the longitudinal axis to open and close jaw member 18.

One or more slots 30 are defined through the inner shaft member 26 and are aligned with one or more corresponding first slots 32 defined through the outer shaft member 28 (FIG. 2). Slots 30 and 32 may include any suitable configuration. In the illustrated embodiment, slots 30 and 32 include a generally elongated configuration. In accordance with the instant disclosure, slots 30 are smaller in length than slots 32, as best seen in FIG. 2. Providing slots 30 with a smaller length allows the outer shaft member 28 to move axially a predetermined distance with respect to the inner shaft member 26 to move the jaw member 18 from an open configuration (FIG. 1) to a closed configuration (not explicitly shown). Specifically, slots 30 are completely filled by resilient fingers 34 on bushing 36 to restrict axial movement of inner shaft member 26. First slots 32 are longer than slots 30 to allow axial movement of outer shaft member 28 to move jaw member 18 from the open configuration to closed configuration. As can be appreciated, first slots 32 can be sized to limit a maximum opening of jaw member 18.

Figure 3:
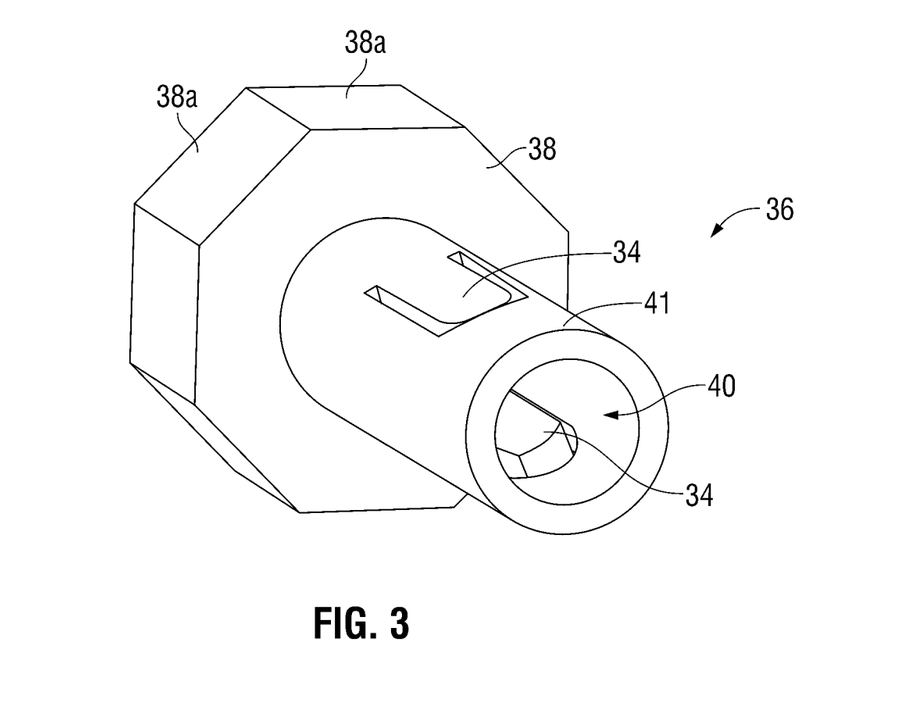
FIG. 3 is a perspective view of a bushing that couples to inner and outer shaft members and to the housing of the endoscopic instrument.

With reference to FIG. 3, a bushing 36 is illustrated including a base 38 and an elongated stem 41 extending distally therefrom. Bushing 36 is configured to fixedly couple to the inner and outer shaft members 26, 28. Accordingly, corresponding mechanical interfaces (e.g., resilient fingers 34) are disposed on stem 41 and are biased radially inward therefrom to engage slots 30 and 32 on the respective inner and outer shaft members 26, 28.

Base 38 is configured to key the bushing 36 to the rotation of the rotating assembly 13. Accordingly, base 38 includes a plurality of planar surfaces 38a (or splines not explicitly shown) that are configured to engage corresponding surfaces of the rotating assembly 13. In the embodiment illustrated in FIG. 3, the base 38 includes eight (8) planar surfaces 38a forming a generally octagonal configuration.

Figure 4:
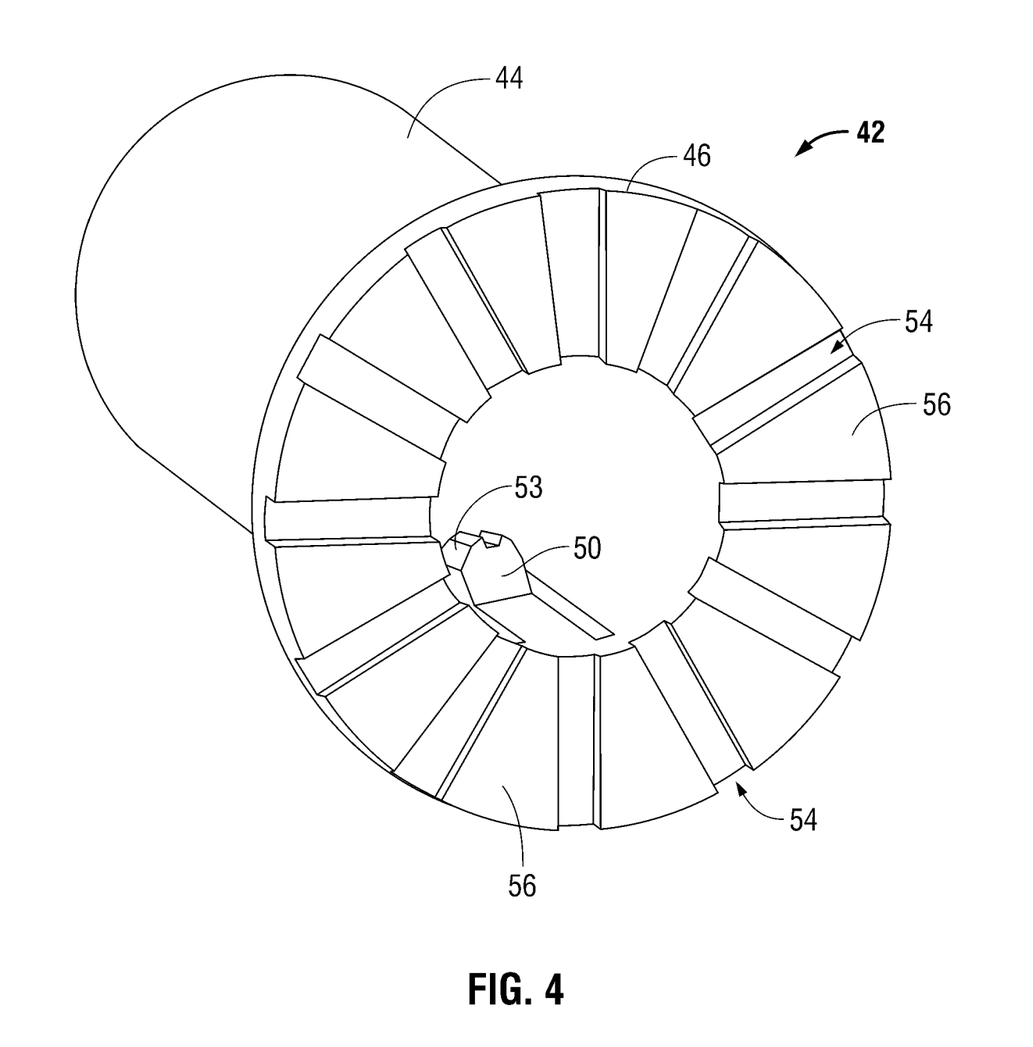
FIG. 4 is a perspective view of a spring carrier that couples to the outer shaft member depicted in FIG. 2.

An aperture 40 of suitable configuration extends through the bushing 36 and is configured to receive the outer shaft member 28 therethrough for coupling the outer shaft member 28 to the spring carrier 42 (FIG. 4).

Spring carrier 42 includes a generally elongated proximal end 44 of suitable configuration that is configured to support a spring (not explicitly shown) thereon (FIG. 4). One or more resilient bosses 50 (one resilient boss 50 illustrated in the drawings) extend radially inward from the elongated proximal end 44 (FIG. 4) and are configured to releasably couple to one or more corresponding slots 52 disposed at the proximal end 12 of the outer shaft member 28 (FIG. 2). The resilient bosses 50 include a chamfered edge 53 (FIG. 4) that is configured to facilitate engaging and disengaging the outer shaft member 28 with the spring carrier 42. In particular, as the outer shaft member 28 is rotated (e.g., counter-clockwise) an edge 15 (FIG. 2) of the outer shaft member 28 that defines the slots 52 cams the resilient boss 50 outwardly.

Spring carrier 42 also includes a generally circumferential distal end 46 that is configured to engage an internal wall (not explicitly shown) of the housing 6. In particular, a plurality of radial slots 54 are formed in a distal face 56 of the spring carrier 42 and are configured to engage corresponding mating features (not explicitly shown) on the internal wall of the of the housing 6. More particularly, when the movable handle 22 is moved proximally, the spring carrier 42 is moved distally toward the distal end of the housing 6 (e.g., the spring carrier 42 is moved to an extreme forward position) and into engagement with the mating features on the internal wall of the housing to "lock" the spring carrier 42 and prevent the spring carrier 42 from rotating with the outer shaft member 28.

In use, after a surgical procedure, e.g., an ultrasonic sealing procedure, has been completed, the bushing 36 including the inner and outer shaft members 26, 28 may be removed so that the housing 6 and ultrasonic shaft coupled thereto may be completely cleaned and re-sterilized by an autoclave. In one embodiment, the moveable handle 22 is moved proximally to move the spring carrier 42 to the extreme forward position to lock the spring carrier 42 as described above. With the spring carrier 42 in the locked position, the outer shaft member 28 may be rotated, e.g., in a counter-clockwise direction, to disengage the resilient bosses 50 from the slots 52 of the outer shaft member 28. Once the resilient bosses 50 are disengaged from the slots 52, the bushing 36 including the inner and outer shaft members 26, 28 may be uncoupled from the housing 6.

To re-attach the bushing 36 including the inner and outer shaft members 26, 28 (or in some embodiments, a new bushing 36 including new inner and outer shaft members 26, 28 with new seals), the bushing 36 including the inner and outer shaft members 26, 28 may be slid over the ultrasonic shaft and the outer shaft member 28 may be reinserted into the spring carrier 42. Once inserted into the spring carrier 42, the outer shaft member 28 may be rotated, e.g., in a clockwise direction, to engage the resilient bosses 50 with the slots 52 of the outer shaft member 28.

The unique configuration of the bushing 36 and shaft assembly 4 of the present disclosure enables a user to quickly and easily couple and uncouple the bushing 36 including the inner and outer shaft members 26, 28 from the housing 6 of the forceps 2 for sterilization of the forceps 2.

With reference to FIGS. 5-10 a shaft assembly 104 according to an alternate embodiment of the present disclosure is illustrated. Forceps 102 and shaft assembly 104 are substantially similar to forceps 2 and shaft assembly 4. In view thereof, only those features unique to the forceps 102 and/or shaft assembly 104 are described in detail.

Figure 5:
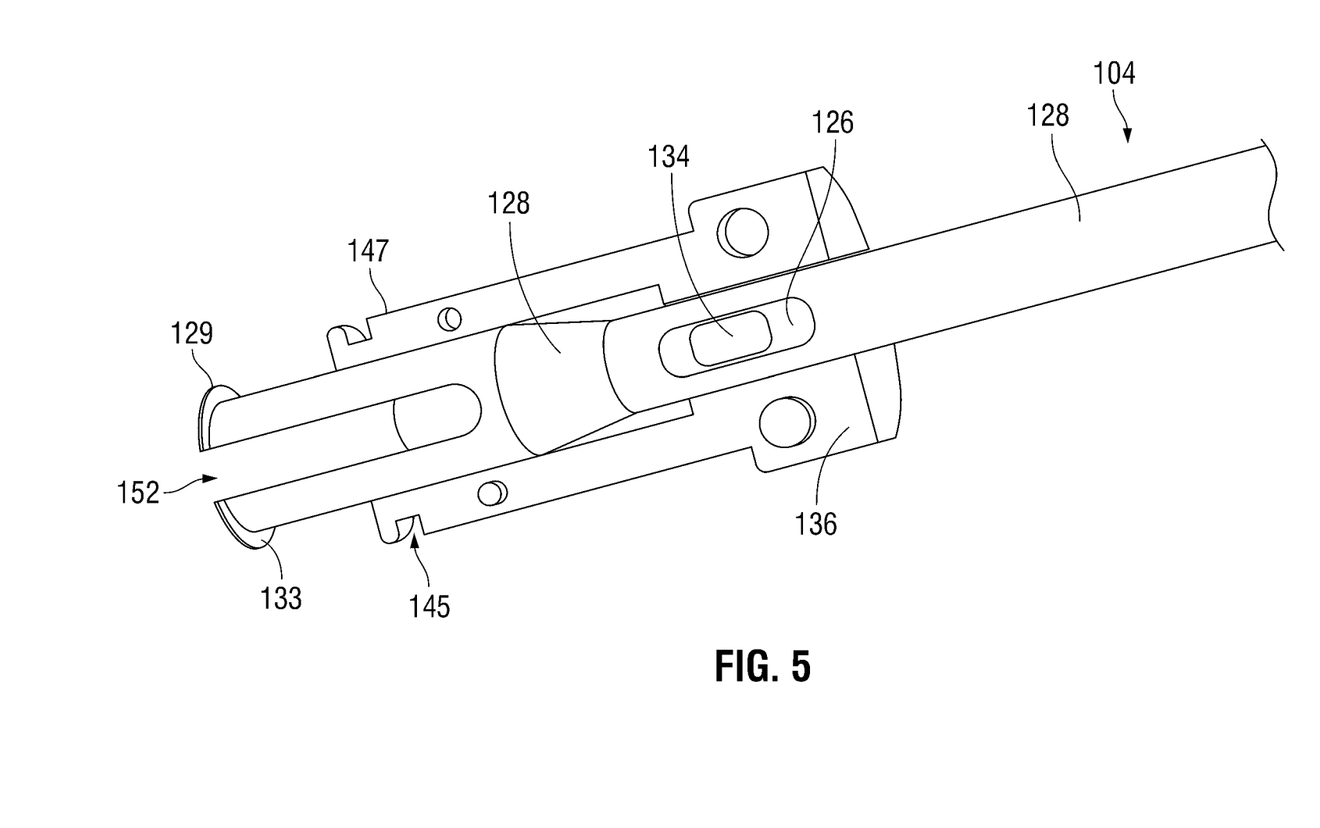
FIG. 5 is a side, perspective view of a selectively removable shaft assembly and bushing coupled thereto according to another embodiment of the instant disclosure.

Unlike outer shaft member 28, outer shaft member 128 includes a proximal flange 129 of suitable configuration (FIG. 5). Proximal flange 129 is configured for engagement with a "guillotine" type locking member 131 that is operably coupled to a spring carrier 142 (FIGS. 6, 8 and 10) to couple the outer shaft member 128 to the spring carrier 142. In one embodiment, the locking member 131 slides over a front face 133 (FIG. 5) of the proximal flange 129 to couple the outer shaft member 128 to the spring carrier 142. This method for coupling the outer shaft member 128 to the spring carrier 142 allows the proximal flange 129 to freely rotate behind the locking member 131 such that the spring carrier 142 does not rotate with the outer shaft member 128.

Figure 10:
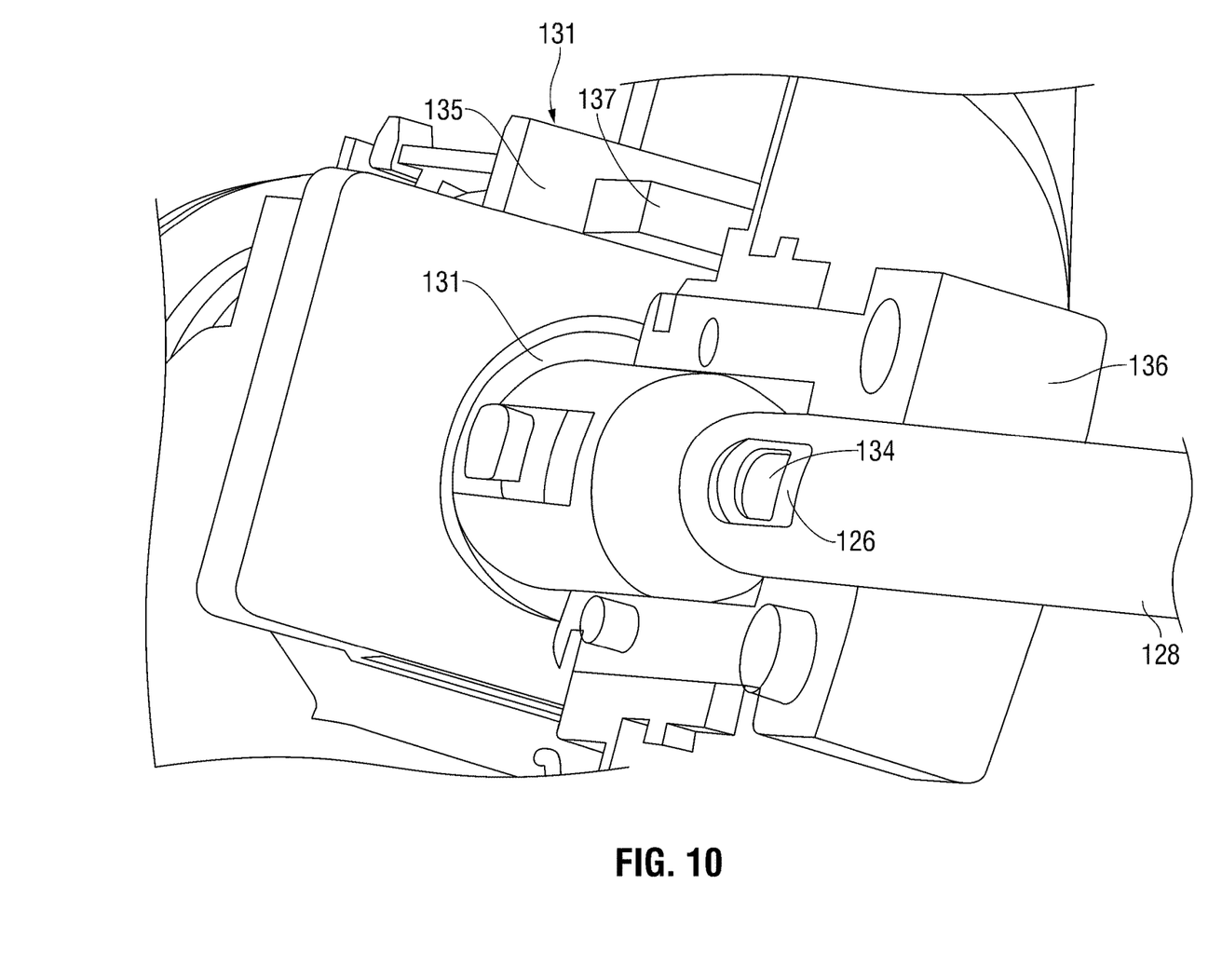
FIG. 10 is the isometric view of FIG. 7 with the latching mechanism removed to illustrate the position of the neighboring components of the latching mechanism when the latching mechanism is in the latched configuration.

Locking member 131 includes a bottom portion with a generally "C-shaped" configuration that rests on an outer surface of the outer shaft member 128, see FIG. 10 for example. This "C-shaped" configuration allows the locking member 131 to move in and out of engagement with the outer shaft member 128 and allows the outer shaft member 128 to move axially with the spring carrier 142.

A top portion 135 (FIGS. 6, 8 and 10) of the locking member 131 includes a detent 137 (FIGS. 6-10) that is configured to engage a corresponding aperture 139 (FIG. 7) on a latch 141 (FIGS. 6-9). The detent 137 and aperture 139 couple the locking member 131 to the latch 141 to allow the locking member 131 and latch 141 to move in unison.

Figure 7:
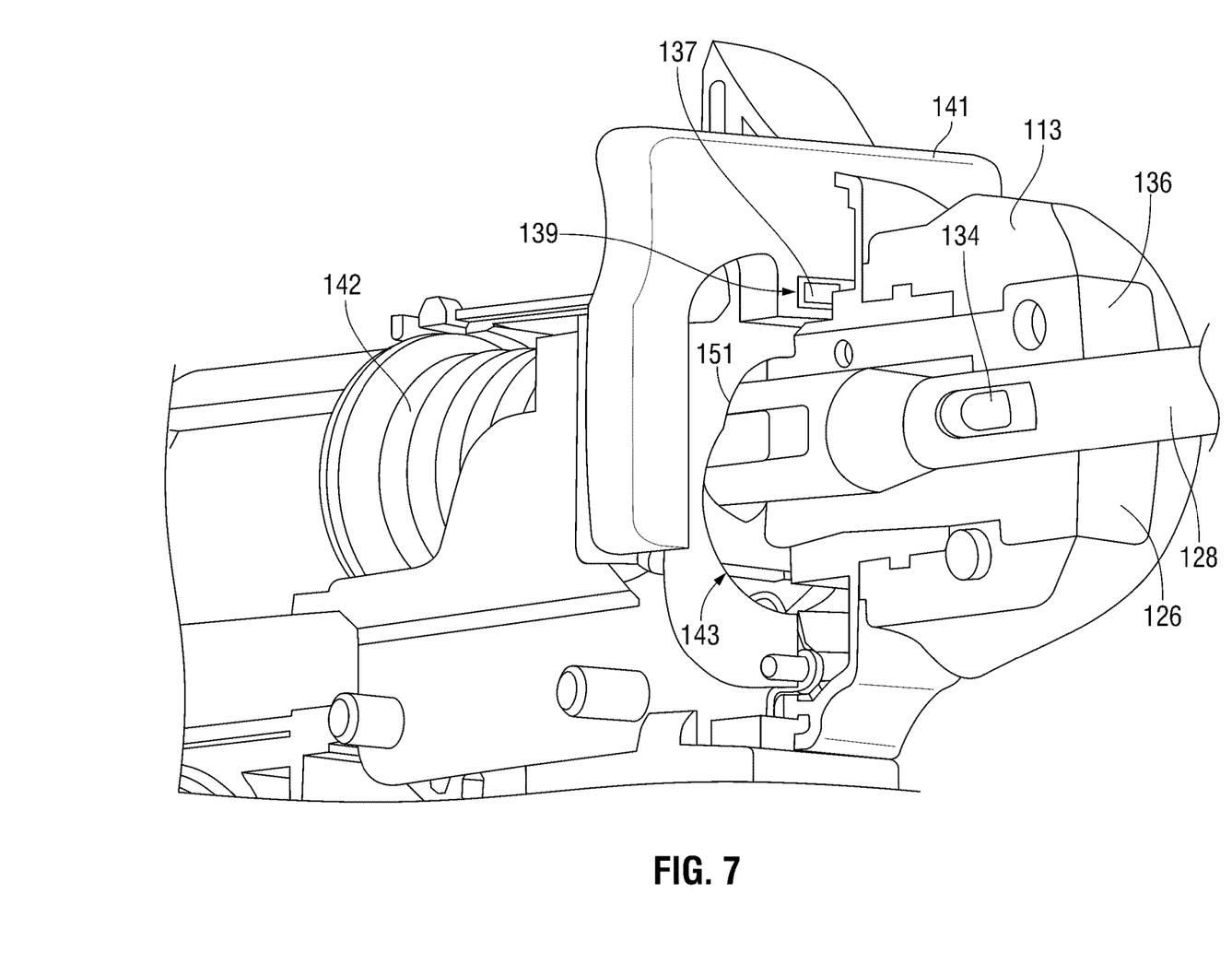
FIG. 7 is an isometric view of the endoscopic instrument depicted in FIG. 6 with a latching mechanism shown in a latched configuration.

The latch 141 is operably disposed in the housing 106 and is accessible to a user from a top portion of the housing 106. The latch 141 also includes an aperture 143 of suitable configuration that allows passage of the bushing 136 including the outer shaft member 128 therethrough (FIGS. 7 and 9).

An interior wall 151 (FIGS. 7 and 9) that defines the aperture 143 is configured to releasably engage an annular groove 145 (as best seen in FIG. 5) disposed at a proximal end 147 of the bushing 136. In particular, pulling the latch 141 a predetermined distance (e.g., upwards) disengages the interior wall 151 from the annular groove 145 and disengages the flange 129 from the locking member 131 so that the bushing 136 including the inner and outer shaft members 126, 128 may be uncoupled from the spring carrier 142. Likewise, pushing the latch 141 a predetermined distance (e.g., downwards) engages the interior wall 151 with the annular groove 145 and engages the flange 129 with the locking member 131 so that the bushing 136 including the inner 126 and outer shaft members 128 may be coupled to the spring carrier 142.

Figure 6:
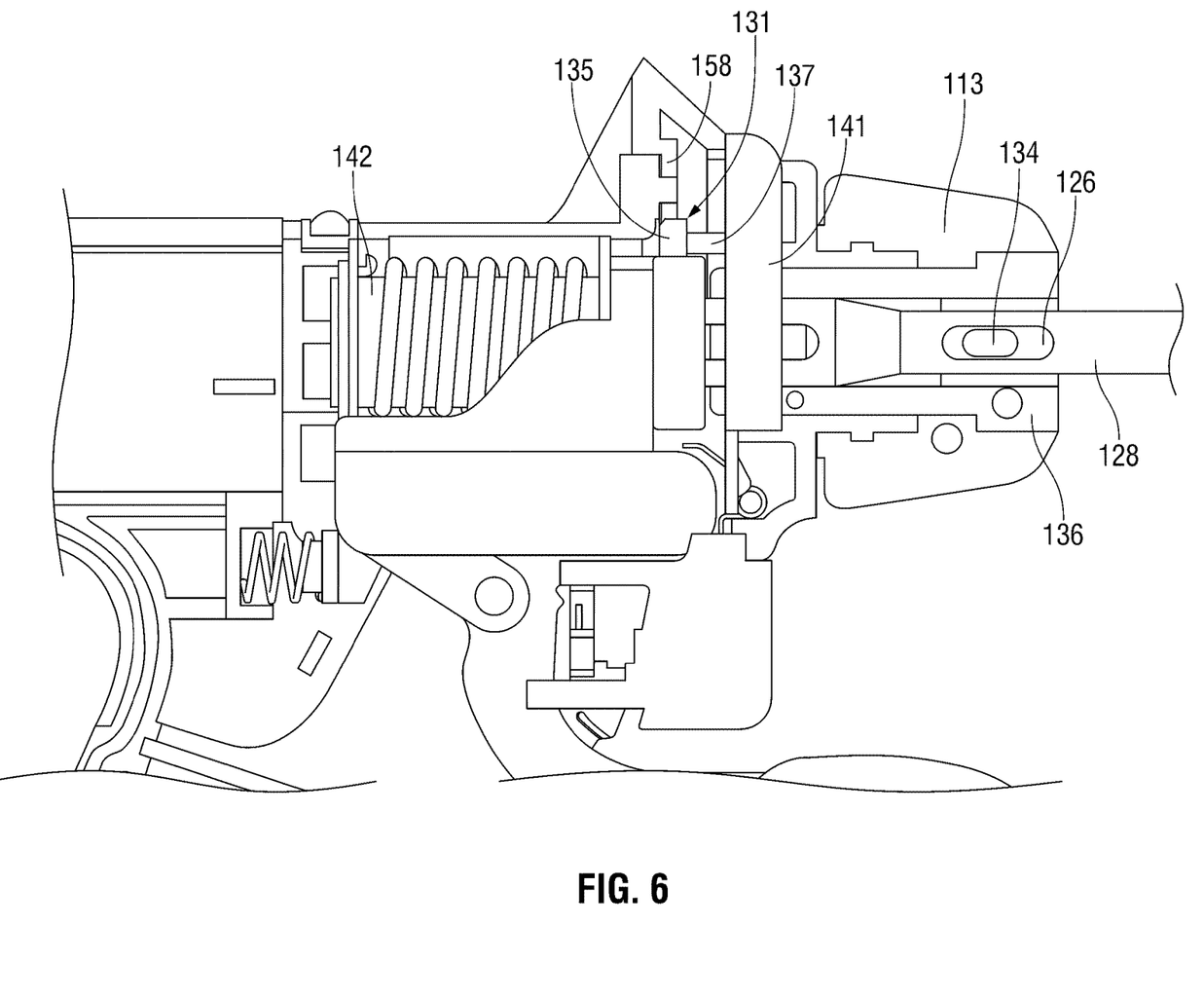
FIG. 6 is a side view of an endoscopic instrument including the selectively removable shaft assembly and bushing depicted in FIG. 5.
Figure 8:
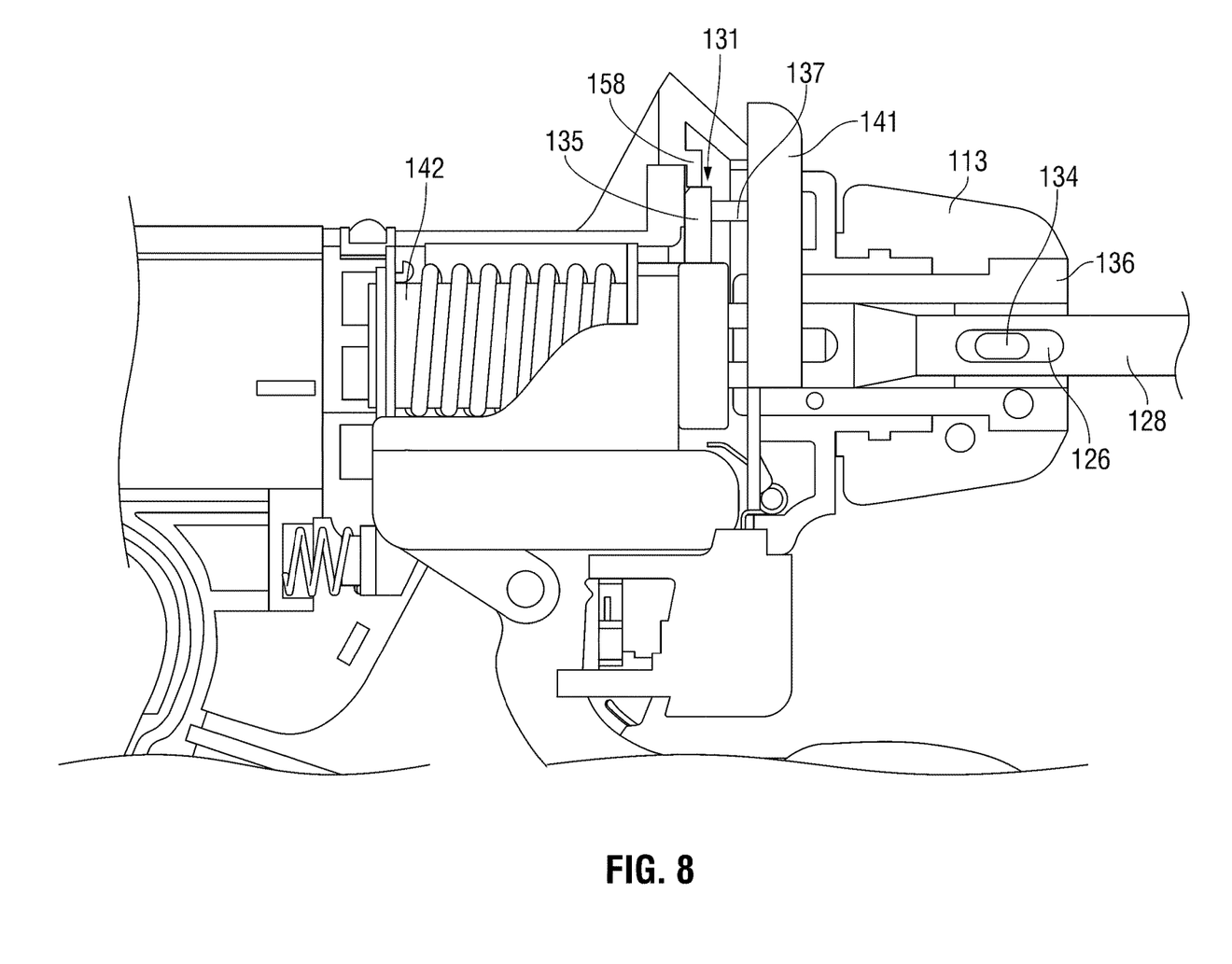
FIG. 8 is a side view of the of the endoscopic instrument depicted in FIG. 6 with the latching mechanism shown in an unlatched configuration.

Unlike bushing 36 that includes a pair of resilient fingers 34, the bushing 136 includes a pair of mechanical interfaces (e.g., detents 134) that are configured to engage corresponding slots 130 and 132, see FIGS. 5, 6 and 8; in these figures, the detent 134 is shown engaged with the slot 130 and as such the slot 130 is not explicitly shown.

Figure 9:
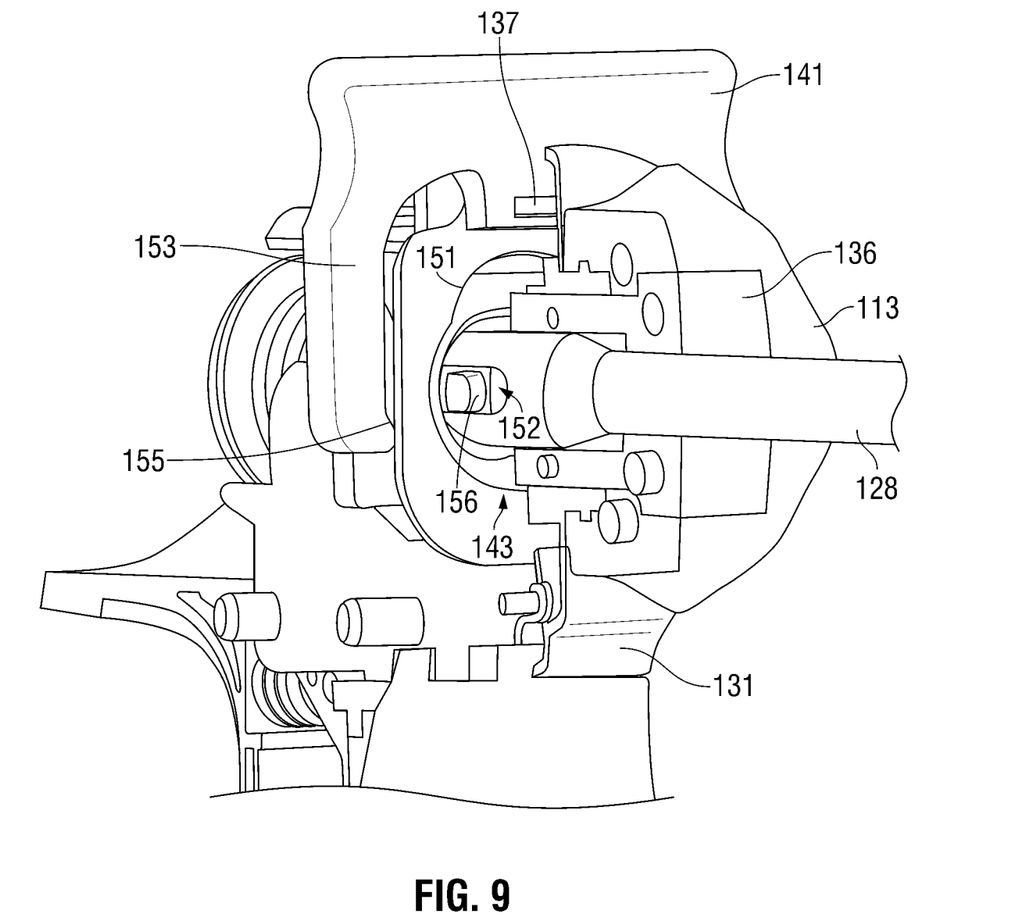
FIG. 9 is an isometric view of the endoscopic instrument depicted in FIG. 8 with the latching mechanism shown in an unlatched configuration.

A guide slot 152 (FIG. 5) is provided to replace slot 52 of the outer shaft member 28 and is configured to engage a corresponding detent 156 that extends from the spring carrier 142 (FIG. 9). This configuration of the guide slot 152 and detent 156 facilitates aligning the annular groove 145 and the inner wall 151 of the locking member 131.

A stop member 158 (FIGS. 6 and 8) defined on an interior surface of the housing 106 is provided and is configured to contact the top surface 135 of the locking member 131 when the latch 141 has been pulled a predetermined distance (e.g., upwards), see FIG. 8 for example; this prevents a user from "over-pulling" the latch 141.

In some embodiments, such as the one illustrated in FIGS. 5-10, the latch 141 includes an optional pair of opposing arms 153 that each include a respective detent 155 (see FIG. 9 for example) that seats within a corresponding pocket (not explicitly shown) disposed within an interior wall of the housing. The detents 155 seated within the pockets are configured to further limit movement of the latch 141.

In use, to uncouple the bushing 136 including inner and outer shaft members 126, 128 from the housing 106, a user pulls the latch 141 (e.g., upwards) to disengage the locking member 131 from the proximal flange 129 and the latch 141 from the annular groove 145.

Once disengaged, the bushing 136 including inner and outer shaft members 126, 128 may be uncoupled from the housing 106.

To re-couple the bushing 136 including inner and outer shaft members 126, 128 to the housing 106, the user re-inserts the bushing 136 including inner and outer shaft members 126, 128 into the housing 106 and pushes the latch 141 (e.g., downwards) to engage the locking 131 member with the proximal flange 129 and the latch 141 with the annular groove 145.

As described above with respect to the bushing 36 and shaft assembly 4, the unique configuration of the bushing 136 and shaft assembly 104 of the present disclosure enables a user to quickly and easily couple and uncouple the bushing 136 including the inner and outer shaft members 126, 128 from the housing 6 of the forceps 102 for sterilization thereof.

From the foregoing and with reference to the various figure drawings, those skilled in the art will appreciate that certain modifications can also be made to the present disclosure without departing from the scope of the same. For example, and as noted above, the ultrasonic shaft may be configured to couple and uncouple with the bushings 36, 136 including inner and outer shafts 26, 126 and 28, 128, respectively. In this instance, one or more components associated with the forceps 2, 102 may be utilized in conjunction with the shaft assemblies 4, 104. For example, in one particular embodiment, a rear knob 3 (FIG. 1) may be utilized to release the ultrasonic shaft. In this instance, the rotating assemblies 13, 113 are held immobile while the rear knob 3 is turned to unscrew the ultrasonic shaft. Once the ultrasonic shaft is unscrewed, it along with the shaft assemblies 4, 104 may be uncoupled as described above.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. An endoscopic instrument, comprising:
   a housing;
   a shaft assembly configured to couple to the housing and including an inner shaft member and an outer shaft member movable relative to the inner shaft member, the inner shaft member defining a slot and the outer shaft member defining a slot;
   a bushing operably coupled to the inner and outer shaft members of the shaft assembly and selectively and releasably coupled to the housing, the bushing including at least one resilient finger configured to engage the slot of the inner shaft member and the slot of the outer shaft member; and
   a spring carrier operably supported within the housing and including at least one resilient boss configured to releasably engage a second slot defined through the outer shaft member, the at least one resilient boss being disengaged from the second slot to release the inner and outer shaft members from the housing when the outer shaft member is rotated with respect to the spring carrier.

2. The endoscopic instrument according to claim 1, wherein the spring carrier includes a plurality of radial slots defined on a distal face thereof, the plurality of radial slots configured to engage a corresponding plurality of mating features disposed on an interior wall of the housing when the spring carrier is moved to a forward position within the housing, wherein engagement between the plurality of radial slots and corresponding plurality of mating features inhibits rotation of the spring carrier when the outer shaft member is rotated, thus facilitating release of the inner and outer shaft members from the housing.

3. The endoscopic instrument according to claim 1, further comprising an end effector operably supported at a distal end of the outer shaft member.

4. The endoscopic instrument according to claim 1, wherein the slot of the outer shaft member is longer than the slot of the inner shaft member such that when the resilient finger of the bushing engages the slot of the outer shaft member and the slot of the inner shaft member, the outer shaft member is able to translate with respect to the inner shaft member.

5. The endoscopic instrument according to claim 1, wherein the endoscopic instrument is an ultrasonic instrument configured to ultrasonically treat tissue.

6. The endoscopic instrument according to claim 1, wherein the at least one resilient boss includes a chamfered edge that is configured to contact an edge of the second slot to move the at least one resilient boss out of engagement with the second slot when the outer shaft member is rotated relative to the spring carrier.

7. The endoscopic instrument according to claim 1, wherein the spring carrier is configured to provide axial movement of the outer shaft member when a handle assembly associated with the housing is actuated.

8. The endoscopic instrument according to claim 1, further comprising a first jaw member operably coupled to the outer shaft member and a second jaw member operably coupled to the inner shaft member, wherein movement of the outer shaft member relative to the inner shaft member causes the first jaw member to pivot relative to the second jaw member.

9. The endoscopic instrument according to claim 8, wherein the slot of the inner shaft member has a smaller length than the slot of the outer shaft member to inhibit movement of the outer shaft member relative to the inner shaft member.

10. An endoscopic instrument, comprising:
    a housing;
    a shaft assembly configured to couple to the housing and including an inner shaft member and an outer shaft member movable relative to the inner shaft member, the outer shaft member defining a slot; and
    a spring carrier operably supported within the housing and including at least one resilient boss configured to releasably engage the slot defined through the outer shaft member, the at least one resilient boss being disengaged from the slot to release the inner and outer shaft members from the housing when the outer shaft member is rotated with respect to the spring carrier, wherein the spring carrier includes a plurality of radial slots defined on a distal face thereof, the plurality of radial slots configured to engage a corresponding plurality of mating features disposed on an interior wall of the housing when the spring carrier is moved to a forward position within the housing, wherein engagement between the plurality of radial slots and corresponding plurality of mating features inhibits rotation of the spring carrier when the outer shaft member is rotated, thus facilitating release of the inner and outer shaft members from the housing.

11. The endoscopic instrument according to claim 10, wherein the endoscopic instrument is an ultrasonic instrument configured to ultrasonically treat tissue.

12. The endoscopic instrument according to claim 10, further comprising a bushing operably coupled to the inner and outer shaft members of the shaft assembly and selectively and releasably coupled to the housing, the bushing including at least one resilient finger configured to engage the inner shaft member and the outer shaft member.

13. The endoscopic instrument according to claim 10, wherein the at least one resilient boss includes a chamfered edge that is configured to contact an edge of the corresponding slot to move the at least one resilient boss out of engagement with the corresponding slot when the outer shaft member is rotated relative to the spring carrier.

14. The endoscopic instrument according to claim 10, further comprising a first jaw member operably coupled to the outer shaft member and a second jaw member operably coupled to the inner shaft member, wherein movement of the outer shaft member relative to the inner shaft member causes the first jaw member to pivot relative to the second jaw member.

* * * * *